(12) United States Patent
Chen et al.

(10) Patent No.: US 10,806,453 B2
(45) Date of Patent: Oct. 20, 2020

(54) STAPLING HEAD ASSEMBLY AND SUTURING AND CUTTING APPARATUS FOR ENDOSCOPIC SURGERY

(71) Applicant: Suzhou Touchstone International Medical Science Co., Ltd., Suzhou (CN)

(72) Inventors: Wangdong Chen, Suzhou (CN); Yongwang Pei, Suzhou (CN)

(73) Assignee: SUZHOU TOUCHSTONE INTERNATIONAL MEDICAL SCIENCE CO., LTD., Suzhou (CN)

( * ) Notice: Subject to any disclaimer, the term of this patent is extended or adjusted under 35 U.S.C. 154(b) by 603 days.

(21) Appl. No.: 15/541,044

(22) PCT Filed: Dec. 30, 2015

(86) PCT No.: PCT/CN2015/099941
§ 371 (c)(1),
(2) Date: Jun. 30, 2017

(87) PCT Pub. No.: WO2016/107586
PCT Pub. Date: Jul. 7, 2016

(65) Prior Publication Data
US 2017/0360439 A1 Dec. 21, 2017

(30) Foreign Application Priority Data

Dec. 30, 2014 (CN) .......................... 2014 1 0842178
Dec. 30, 2014 (CN) .................... 2014 2 0858637 U

(51) Int. Cl.
*A61B 17/72* (2006.01)
*A61B 17/072* (2006.01)
(Continued)

(52) U.S. Cl.
CPC .. *A61B 17/07207* (2013.01); *A61B 17/00234* (2013.01); *A61B 17/0469* (2013.01);
(Continued)

(58) Field of Classification Search
CPC ........ A61B 17/07207; A61B 17/00234; A61B 17/0469; A61B 17/320016;
(Continued)

(56) References Cited

U.S. PATENT DOCUMENTS 7,543,730 B1  6/2009  Marczyk
2006/0226195 A1  10/2006  Scirica et al.
(Continued)

FOREIGN PATENT DOCUMENTS

AU  2013203114 A1  5/2013
CN  201879758 U  6/2011
(Continued)

OTHER PUBLICATIONS

Chinese Office Action for application No. 201410842178.0 dated Sep. 29, 2017, 9 pages.
(Continued)

*Primary Examiner* — Chelsea E Stinson
*Assistant Examiner* — Mary C Hibbert-Copeland
(74) *Attorney, Agent, or Firm* — Cantor Colburn LLP

(57) ABSTRACT

A stapling head assembly includes a cartridge support having a proximal end, a connecting tube, a cutter pushing rod, and a lockout mechanism. The tube includes a distal end connected to the proximal end. The rod is movably set inside the tube. The mechanism is connected to the tube, and includes a pressing block and a pushing block. The pressing block is used to lock the proximal end to prevent the rod from moving before the assembly is used. The pressing block is rotatable between a first position and a second position relative to the tube. The pushing block is used to
(Continued)

push the pressing block to rotate from the first position towards the second position. The pushing block is located at one side of the pressing block, and is movable between a third position and a fourth position relative to the tube along a longitudinal direction.

18 Claims, 6 Drawing Sheets

(51) Int. Cl.
   *A61B 17/00* (2006.01)
   *A61B 90/00* (2016.01)
   *A61B 17/04* (2006.01)
   *A61B 17/32* (2006.01)
(52) U.S. Cl.
   CPC ............ *A61B 17/320016* (2013.01); *A61B 2017/00473* (2013.01); *A61B 2017/07271* (2013.01); *A61B 2017/07278* (2013.01); *A61B 2017/07285* (2013.01); *A61B 2090/034* (2016.02); *A61B 2090/038* (2016.02); *A61B 2090/0801* (2016.02)
(58) Field of Classification Search
   CPC ........... A61B 2017/00473; A61B 2017/07271; A61B 2017/07278; A61B 2017/07285
   USPC .......................................... 227/175.1–180.1
   See application file for complete search history.

(56) References Cited

U.S. PATENT DOCUMENTS

| | | |
|---|---|---|
| 2008/0179375 A1 | 7/2008 | Scirica |
| 2013/0140342 A1 | 6/2013 | Milliman et al. |
| 2014/0358129 A1 | 12/2014 | Zergiebel et al. |

FOREIGN PATENT DOCUMENTS

| | | | |
|---|---|---|---|
| CN | 202113112 U | 1/2012 | |
| CN | 102599954 A | 7/2012 | |
| CN | 102697532 A | 10/2012 | |
| CN | 202982105 U | 6/2013 | |
| CN | 103860221 A | 6/2014 | |
| CN | 103860223 A | 6/2014 | |
| CN | 204364050 U | 6/2015 | |
| EP | 1563794 A1 | 8/2005 | |
| EP | 1774914 A1 | 4/2007 | |
| EP | 1300117 B1 | 8/2007 | |
| EP | 1813197 A2 | 8/2007 | |
| EP | 2138109 A2 * | 12/2009 | ....... A61B 17/07207 |
| EP | 2138109 A2 | 12/2009 | |
| WO | 0243582 A1 | 6/2002 | |

OTHER PUBLICATIONS

European Search Report for application No. 15875262.6 dated Nov. 13, 2017; 8 pages.
International Search Report for application No. PCT/CN2015/099941 dated Mar. 21, 2016, 4 pages.

* cited by examiner

STAPLING HEAD ASSEMBLY AND SUTURING AND CUTTING APPARATUS FOR ENDOSCOPIC SURGERY

CROSS-REFERENCES TO RELATED APPLICATIONS

This patent application is a 371 of International Application No. PCT/CN2015/099941, filed Dec. 30, 2015 which claims the priority of Chinese Application No. 201420858637.X, filed Dec. 30, 2014 and Chinese Application No. 201410842178.0, filed Dec. 30, 2014, each of which are incorporated herein by reference in their entirety.

TECHNICAL FIELD

The invention relates to the field of medical instruments, particularly, to a stapling head assembly with a lockout mechanism preventing from being fired by mistake and a suturing and cutting apparatus for endoscopic surgery with the stapling head assembly.

BACKGROUND

A suturing and cutting apparatus for surgery has been widely used for suturing wounds, suturing and cutting internal tissues. The surgery having developed so far has an increasing tendency to be minimally invasive surgery. Generally speaking, minimally invasive surgery means all operations which can decrease wounds; narrowly speaking, minimally invasive surgery means the operations processed under endoscope. Generally, only a few small holes are needed to be opened on the patient's body for an operation for endoscopic surgery, so the cutting and suturing instruments and assistant instruments can be used for operation by going into the patient's body through the small holes. With the little wounds caused from the minimally invasive surgery, the patients can recover in a very short time, so the minimally invasive surgery has gotten more and more attention.

The liner suturing and cutting apparatus for endoscopic surgery used in minimally invasive surgery in the existing technology, comprises an instrument body, said instrument body comprises a sleeve and an actuating handle pivotally connected to the sleeve, there is an actuating rod removable set in the sleeve, said stapling head assembly at the front end of the sleeve can be pushed by said actuating rod to process suturing and cutting. Specifically, said stapling head assembly comprises a cartridge support, and an anvil pivotally connected to the cartridge support. There is a cartridge detachably set on the cartridge support. The stapling head assembly also comprises a cutter pushing rod set movably in the connecting tube of the stapling head assembly and cooperate and connect with a actuating rod, there is a blade set at the distal end of the cutter, and the cartridge and the anvil are closed during the advancing process of the cutter, then the tissues between the cartridge and the anvil are cut off, and the actuating block is actuated to push staple pushers out of the cartridge in a sequence, then the staples are pushed out of the cartridge by the staple pushers and are stapled on the tissues.

In the existing technology, the operation can be processed only after the cartridge assembly is mounted to the instrument platform (which is the body) of the suturing and cutting apparatus for endoscopic surgery. However, before the cartridge assembly is mounted to the instrument platform of the suturing and cutting apparatus for endoscopic surgery, the cutter pushing rod may begin to move during the processes of assembling, packaging, transportation and so on, then the cutter is driven by the cutter pushing rod, and the instrument will be fired by mistake, and due to the movement of cutter pushing rod, the instrument platform will not mount correctly with the cutter pushing rod, and the instrument cannot be used normally as a result.

SUMMARY

The object of the present disclosure provides a stapling head assembly and a suturing and cutting apparatus for endoscopic surgery, which can prevent the cutter pushing rod from moving during the processes of assembling, packaging, transportation and so on, and prevent the instrument from being fired by mistake.

One aspect of the invention provides a stapling head assembly, said stapling head assembly comprises: a cartridge support, equipped detachably with a cartridge; a connecting tube, the distal end thereof connects to the proximal end of said cartridge support; a cutter pushing rod, set movably inside said connecting tube; and a lockout mechanism, connecting to said connecting tube, said lockout mechanism comprises: a pressing block, used to lock the proximal end of said cutter pushing rod, to prevent said cutter pushing rod from moving before said stapling head assembly is used, said pressing block is rotatable between a first position and a second position relative to said connecting tube; and a pushing block, used to push said pressing block to rotate from said first position towards said second position, said pushing block is located at one side of said pressing block, and is movable between a third position and a fourth position relative to said connecting tube along the longitudinal direction thereof.

In an embodiment, a first blocking portion is set at the proximal end of the cutter pushing rod, a second blocking portion is set on said pressing block, when said pressing block is located at said first position, said second blocking portion clamps with said first blocking portion, said cutter pushing rod cannot move under a locking status; when said pressing block rotates to said second position, said second blocking portion departs from said first blocking portion, said cutter pushing rod is under an unlocking status and is movable along the longitudinal direction.

In another embodiment, said pushing block is set at the periphery of the connecting tube, when said pushing block moves from said third position to said fourth position, the pressing block is pushed to rotate from said first position to said second position.

In another embodiment, there is a first limiting groove set at a side wall of said connecting tube along the longitudinal direction thereof, said pressing block connects to the inside of said first limiting groove by a pin, said pressing block is rotatable around said pin relative to said connecting tube.

In another embodiment, the proximal end of said pressing block connects to said connecting tube by said pin, said second blocking portion is set at the distal end of said pressing block.

In another embodiment, there is further a second limiting groove set on said connecting tube along the longitudinal direction thereof, said second limiting groove is set at one side of said first limiting groove, and communicates to said first limiting groove, said pushing block is set inside said second limiting groove, and is moveable between said third position and the fourth position along said second limiting groove.

In another embodiment, said lockout mechanism further comprises: a torsional spring, connecting said pressing block and said connecting tube, actuating said pressing block to rotate from said second position to said first position; and a spring, connecting said pushing block and said connecting tube, actuating said pushing block to move from said fourth position towards the direction of said third position.

In another embodiment, the proximal end of said spring connects to the distal end of said pushing block, and the distal end of said spring connects to said connecting tube.

In another embodiment, one end of said torsional spring connects to said pressing block, and the other end connects to the inner wall of said connecting tube.

In another embodiment, there is a first guiding portion at the outer surface of said pushing block, there is a second guiding portion set at the side wall of one side of the distal end of said pressing block close to said pushing block, said second guiding portion is set at the outer surface of said pushing block, when said pushing block moves from said third position to said fourth position, said first guiding portion pushes said second guiding portion, so said pressing block rotates from said first position to said second position.

In another embodiment, said first guiding portion is a first slope, said first slope orients to the distal end of said pushing block, and inclines upwards from the distal end to the proximal end.

In another embodiment, said second guiding portion is a bump set protruded at a side wall of the distal end of said pressing block.

In another embodiment, there is further a third guiding portion set at the proximal end of said cutter pushing rod, when said cutter pushing rod moves to the proximal end of said connecting tube, said third guiding portion guides said pressing block to rotate from said first position to the second position.

In another embodiment, said third guiding portion is a second slope, said second slope orients towards the proximal end of said cutter pushing rod, and inclines downwards from the distal end to the proximal end.

By utilizing the stapling head assembly and the suturing and cutting apparatus of the present disclosure for endoscopic surgery, the cutter pushing rod can be effectively prevented from moving during the processes of assembling, packaging, transportation and so on before the cartridge assembly is mounted onto the instrument platform of the endoscopic stapler, and prevent the instrument from being fired by mistake, and the instrument platform can be made sure to be mounted correctly with the cutter pushing rod before operation.

BRIEF DESCRIPTION OF THE FIGURES

By reading of the detailed description of the nonrestrictive embodiments referring to the figures following, the other technical features, objective and advantages will be more apparent:

FIG. 3b is a partial enlarged view of the position A of FIG. 3a;

FIG. 5b is a partial enlarged view of the position B of FIG. 5a; and

DETAILED DESCRIPTION

Figure 1:
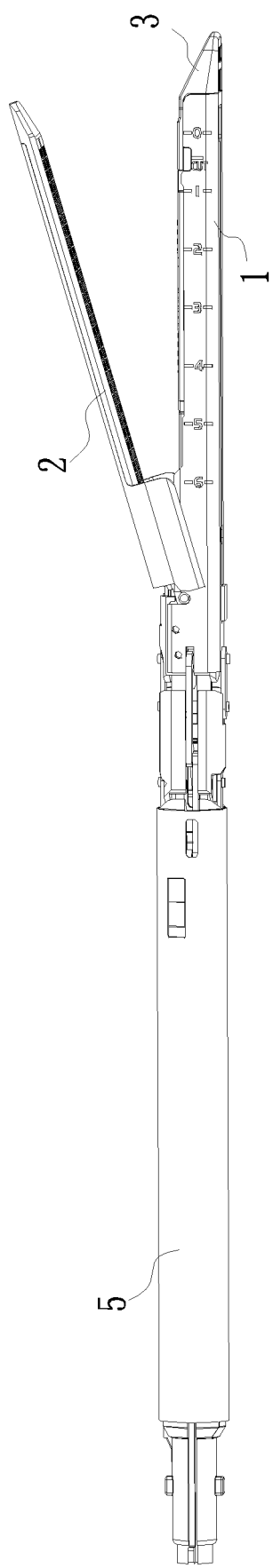
FIG. 1 is a stereoscopic view of the stapling head assembly of the invention.

The description of the proximal end and the distal end, all refer to the operator of the instrument, the proximal end is the end close to the operator, and the distal end is the end far from the operator. The longitudinal direction of the invention means the direction of length of the component, generally the direction from the distal end to the proximal end. The descriptions of direction or position like top/up, bottom/down, vertical, horizontal and so on are descriptions using the figures as examples, and can be changed according to different requirements; the changes made are all included in the protection scope of the invention. Besides, the terms first, second, third, fourth and so on are only for description, cannot be understood to indicate or imply relative significance or imply the numbers of the technical features indicated.

According to the conception of the purport, the stapling head assembly comprises a cartridge support, an anvil, a cartridge, an actuating block, a connecting tube, a cutter pushing rod, a cutter and a lockout mechanism. The cartridge support is equipped detachably with a cartridge; the anvil can pivot and move relatively close to the cartridge; the actuating block is set movably inside the cartridge; the distal end of the connecting tube connects to the proximal end of said cartridge support; the cutter pushing rod is set detachably inside said connecting tube, there is a first blocking portion set at the proximal end of said cutter pushing rod, there is a cutter set at the distal end of said cutter pushing rod, said cutter is pushed by said cutter pushing rod to push said actuating block to move; and a lockout mechanism, connecting to said connecting tube, said lockout mechanism comprises: a pressing block, there is a second blocking portion set on said pressing block, and said pressing block is rotatable relative to said connecting tube between a first position and a second position, when said pressing block is set at said first position, said second blocking clamps with said first blocking portion, said cutter pushing rod cannot move under a locking status, when said pressing block rotates to said second position, said second blocking portion departs from said first blocking portion, said cutter pushing rod is under an unlocking status and is movable along the longitudinal direction; and a pushing block, set at the periphery of the proximal end of the connecting tube, located at one side of said pressing block, and being able to move between a third position and a fourth position relative to said connecting tube along the longitudinal direction thereof, when said pushing block moves from said third position to said fourth position, the pressing block is pushed to rotate from said first position to the second position.

Below the technical contents of the invention are further illustrated combining the figures and embodiments:

Referring to FIG. 1 to FIG. 4 together, which show separately a stereoscopic view, an explosive view, a stereoscopic view under the locking status and a schematic view of the connection relationship of the pressing block and the cutter pushing rod when the stapling head assembly is under the locking status. Wherein, as the cartridge support, anvil, cartridge and actuating block of the stapling head assembly are not a part of the innovations of the invention, so, to show the structure of the stapling head assembly more clearly, apart from FIG. 1, in other figures, the cartridge support, anvil, cartridge and actuating block of the stapling head assembly are all ignored. In an embodiment of the invention, the stapling head assembly may comprise: a cartridge support 1, an anvil 2, a cartridge 3, an actuating block (not shown), a connecting tube 5, a cutter pushing rod 6, a cutter 7 and a lockout mechanism.

As shown in FIG. 1, the anvil 2 may connect to the upward side of the cartridge support 1 and the proximal end of the anvil 2 may pivotally connect to the cartridge support 1. The cartridge 3 is set between the cartridge support 1 and the anvil 2, and detachably connects to the cartridge support 1. There are staple holes for accommodating staple pushers and staples set inside the cartridge 2, generally there are 4 raws or 6 raws staple holes.

Figure 2:
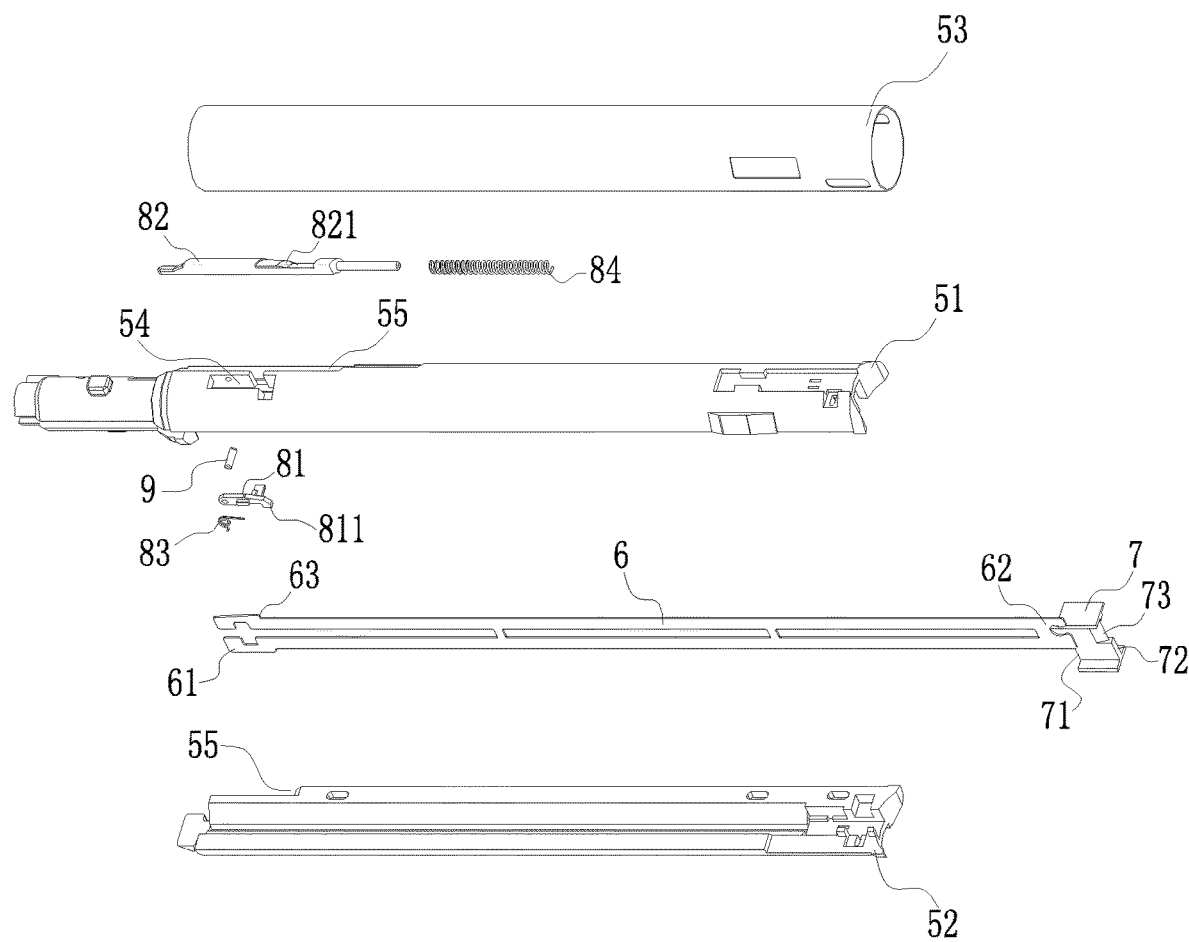
FIG. 2 is an explosive view of the stapling head assembly of the invention.

The distal end of the connecting tube 5 connects to the proximal end of the cartridge support 1. As shown in FIG. 2, the connecting tube 5 comprises an upper support component 51, a lower support component 52 jointed with each other and an annular tube 53 set to cover the upper support component 51 and the lower support component 52.

There is a first limiting groove 54 and a second limiting groove 55 set at the proximal end of the connecting tube 5. In the embodiment shown in FIG. 3a, the first limiting groove 54 may be set at the side wall of the proximal end of the upper support component 51. The second limiting groove 55 is set at the proximal end of the junction of the upper support component 51 and the lower support component 52, the second limiting groove 55 is set along the longitudinal direction of the connecting tube 5, the second limiting groove 55 is set at one side of the first limiting groove 54, and communicates with the first limiting groove 54.

The cutter pushing rod 6 is set in the connecting tube 5 movably. Specifically, the cutter pushing rod 6 is set between the upper connecting component 51 and the lower connecting component 52. There is a first blocking portion 63 set protruded at the top portion of the proximal end 61 of the cutter pushing rod 6, the distal end 62 of the cutter pushing rod 6 connects to the proximal end 71 of the cutter 7. There is further a blade 73 set at the distal end 72 of the cutter 7. During the process of said cutter pushing rod 6 pushing said cutter 7 to move towards the distal end, the tissues between the anvil 2 and the cartridge 3 can be cut off by the blade 73, meanwhile, the cutter 7 can push the actuating block to move, then the staple pushers are pushed out of the cartridge 3 in sequence, then the staples are pushed out of the cartridge 3 and stapled onto the tissues. In the embodiment, the longitudinal section of the cutter 7 is I-shaped, during the process of the cutter pushing rod 6 pushing the cutter 7 to move towards the distal end, the I-shaped cutter 7 can actuate the anvil 2 close to the cartridge 3.

The lockout mechanism connects to the proximal end of the connecting tube 5; the lockout mechanism comprises a pressing block 81, a pushing block 82, a torsional spring 83 and a spring 84.

Figure 3A:
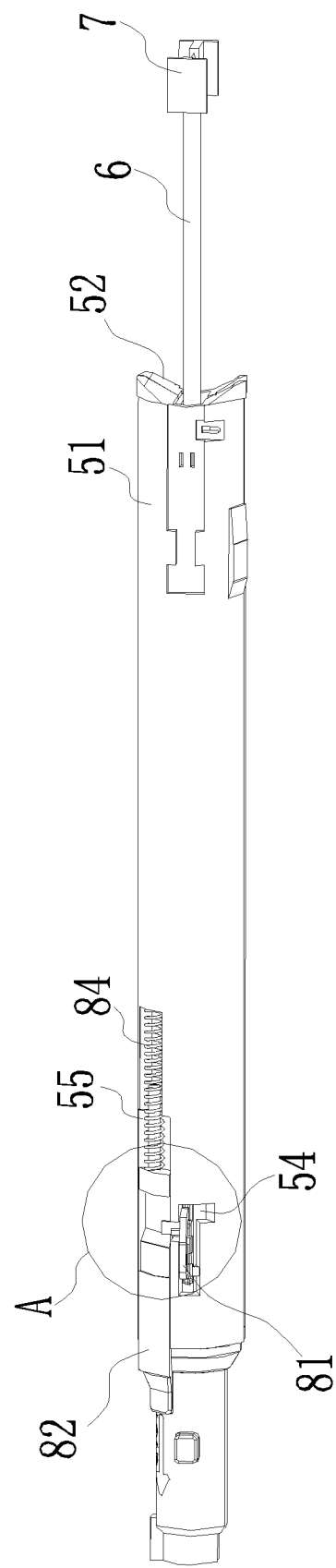
FIG. 3a is a stereoscopic view of the stapling head assembly of the invention under a locking status.
Figure 3B:
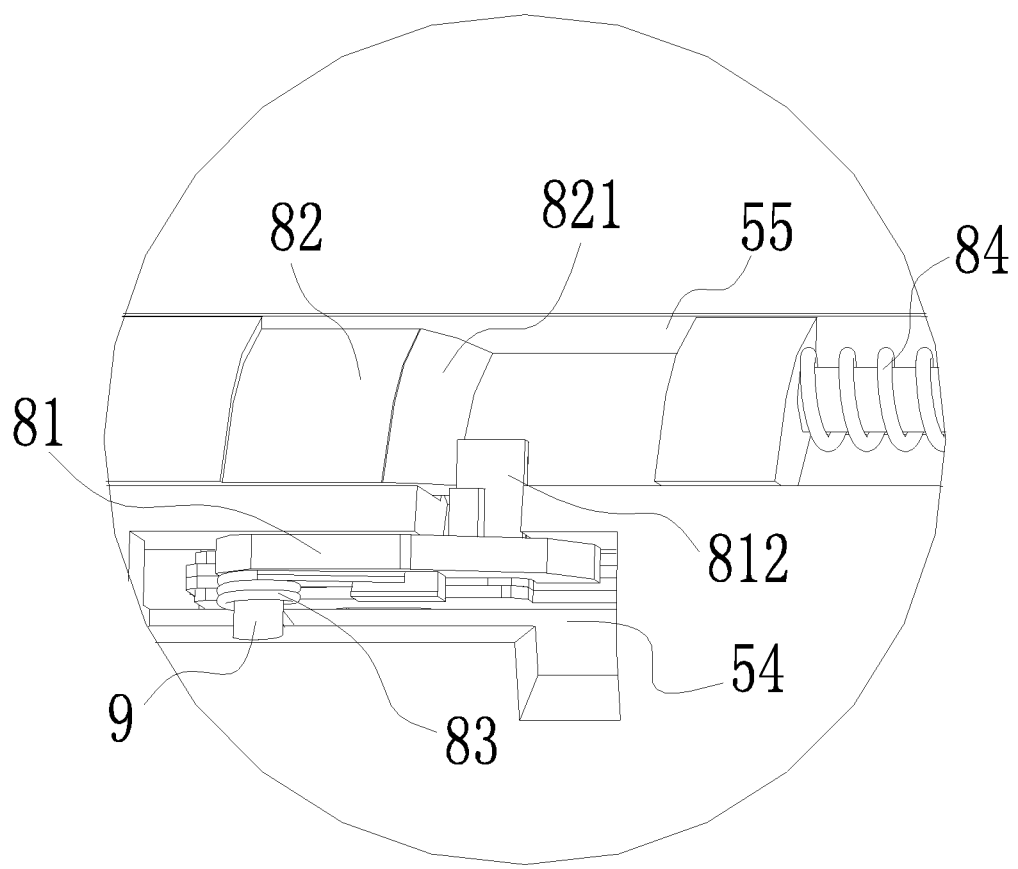
Figure 4:
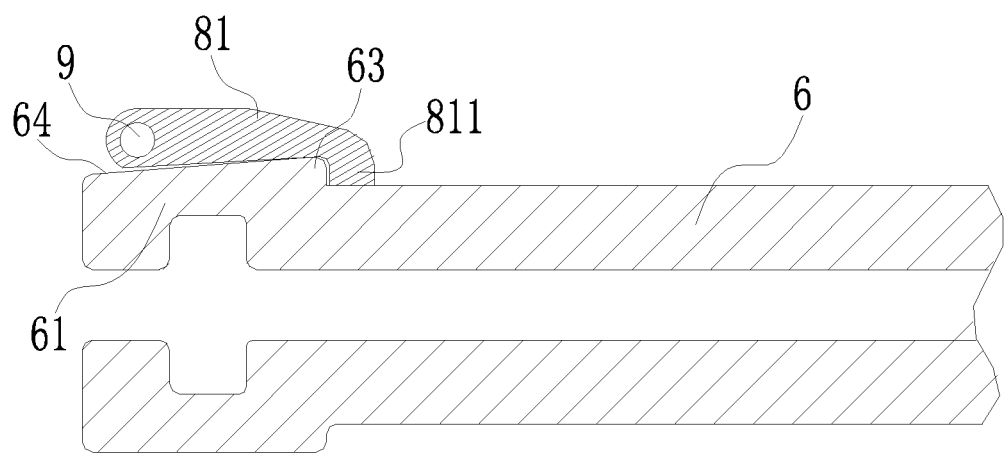
FIG. 4 is a schematic view of the connection relationship of the pressing block and the cutter pushing rod when the stapling head assembly is under a locking status.
Figure 6:
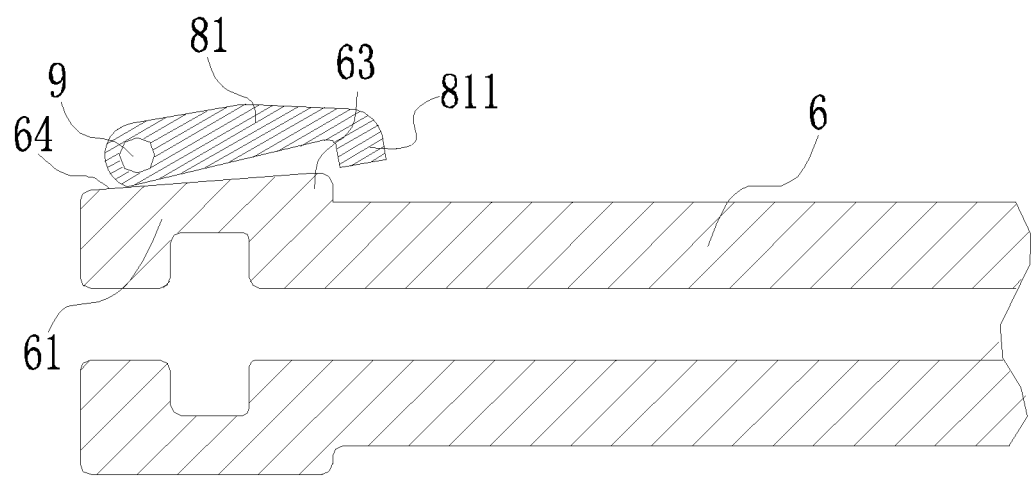
FIG. 6 is a schematic view of the connection relationship of the pressing block and the cutter pushing rod when the stapling head assembly is under an unlocking status.

There is a second blocking portion 811 set on the pressing block 81, and the pressing block 81 is rotatable between a first position and a second position relative to the connecting tube 5, when the pressing block 81 is located at the first position (the position of the pressing block 81 in FIG. 4 is the first position), the second blocking portion 811 of the pressing block 81 clamps with the first blocking portion 63 of the cutter pushing rod 6, then the cutter pushing rod 6 cannot move and is under the locking status, when the pressing block 81 rotates to the second position (the position of the pressing block 81 in FIG. 6 is the second position), the second blocking portion 811 departs from the first blocking portion 63, the cutter pushing rod 6 can be moved and under the unlocking status. In the embodiment, the rotating of the pressing block 81 from the first position to the second position is equivalent to the anticlockwise rotation of the pressing block 81 from the position shown in FIG. 4. As shown in FIG. 3a and FIG. 3b, the pressing block 81 set in the first limiting groove 54 by a pin 9, the proximal end of the pressing block 81 is rotatable around the pin 9 relative to the connecting tube 5. The second blocking portion 811 is set at the distal end of the pressing block 81.

The pushing block 82 is set at the periphery of the connecting tube 5, and located at one side of the pressing block 81, and is movable between a third position and a fourth position relative to the connecting tube 5 along the longitudinal direction thereof, when the pushing block 82 moves from the third position to the forth position, the pressing block 81 is pushed to move from the first position to the second position. As shown in FIG. 3a and FIG. 3b, the pushing block 82 is set inside the second limiting groove 55, and is movable along the second limiting groove 55 between the third position and the fourth position, the position of the pushing block 82 in FIG. 3b is the third position, this moment, the pressing block 81 cooperates with the distal end of the pushing block 82, and the second blocking position 811 of the pressing block 81 clamps with the first blocking portion 63 of the cutter pushing rod 6; the position of the pushing block 82 shown in FIG. 5b is the fourth position, this time, the pressing block 81 cooperates with the proximal end of the pushing block 82, and the second blocking portion 811 of the pressing block 81 departs from the first blocking portion 63 of the cutter pushing rod 6; the third position is located at the proximal end of the fourth position.

The torsional spring 83 connects the pressing block 81 and the connecting tube 5 by a pin 9, and actuates the pressing block 81 to rotate from the second position towards the first position. In the embodiment, one end of the torsional spring 83 connects to the pressing block 81, and the other end connects to the inner wall of the upper support component 51.

The spring 84 connects to the pushing block 82 and the connecting tube 5, and actuates the pushing block 82 to move from the fourth position towards the direction of the third position. As shown in FIG. 3b, the proximal end of the spring 84 connects to the distal end of the pushing block 82; the distal end of the spring 84 connects to the side wall of the upper support component 51. The technicians in the art should understand, in some embodiments, the flexible portion can be changed, such as, the flexible portion can be a flexible block set between the pushing block 82 and the side wall of the upper support component 51. It won't be described in detail here.

Referring to FIG. 3b, and before the stapling head assembly is unlocked, the pressing block 81 is located at the first position, the pushing block 82 is located at the third position. There is a second guiding portion 812 set on the side wall of one side of the distal end of the pressing block 81 close to the pushing block 82, the second guiding portion 812 contacts the outer surface of the pushing block 82, the second guiding portion 812 may be a bump set protruded on the side wall of the distal end of the pressing block 81. The bump extends out from the side surface of the pressing block 81, and passes through the communication position of the first limiting groove 54 and the second limiting groove 55, and contacts the outer surface of the pushing block 82. There is a first guiding portion 821 at the outer surface of the pushing block 82, when the pushing block 82 moves from the third position to the fourth position, the first guiding portion 821 is used to push the second guiding portion 812, and actuates the pressing block 81 to rotate from the first position to the second position, the first guiding portion 821 is a first slope, the first slope inclines upwards from the distal end to the proximal end of the pushing block 82, as shown in FIG. 3b, the first slope is close to the proximal end of the bump.

Figure 5A:
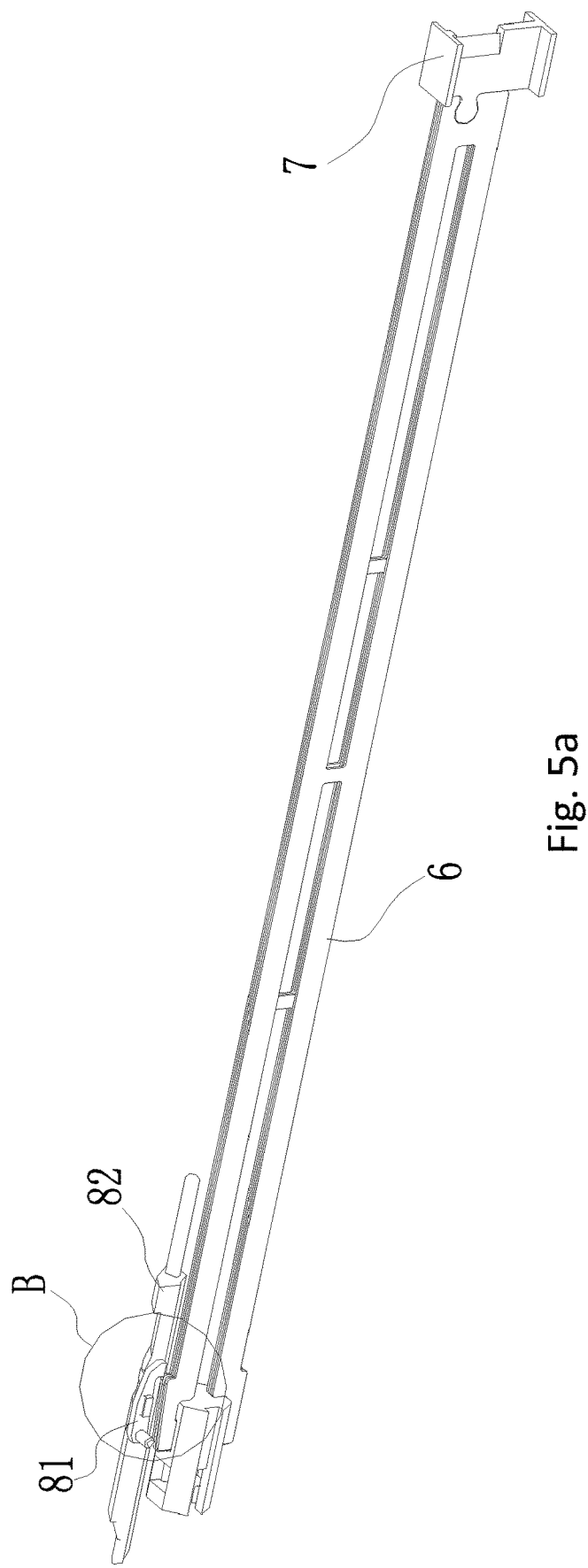
FIG. 5a is a stereoscopic view of the stapling head assembly of the invention under an unlocking status.
Figure 5B:
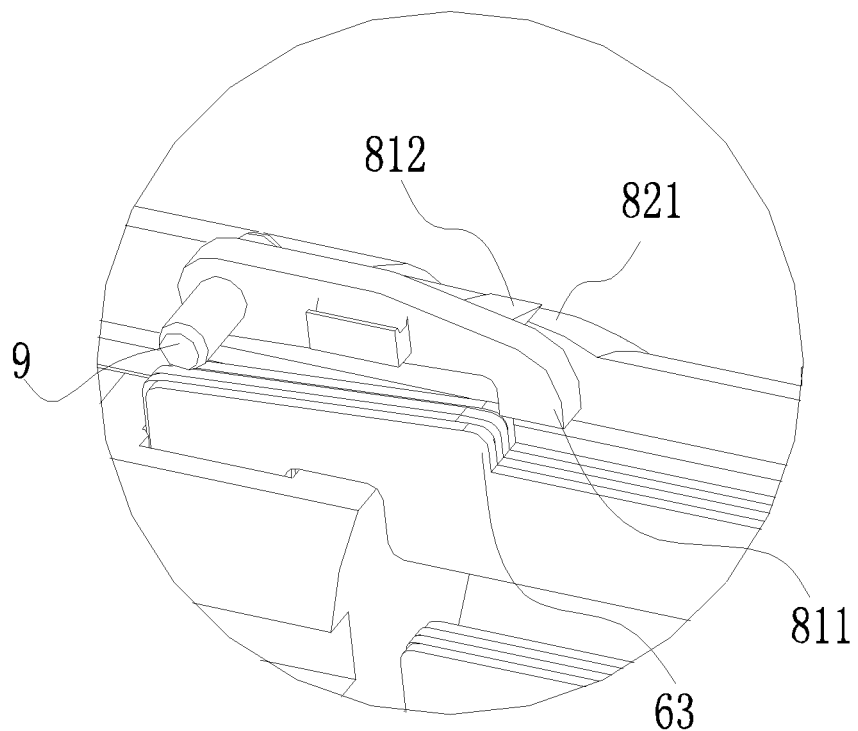

Furthermore, referring to FIG. 5a, FIG. 5b and FIG. 6 together, which show separately a stereoscopic view of the stapling head assembly under the unlocking status and a schematic view of the connection relationship of the pressing block and the cutter pushing rod. The connecting tube 5 is ignored in FIG. 5a and FIG. 5b to more clearly show the structure of the lockout mechanism. As shown in FIG. 3b, during the process of the stapling head assembly being mounted to the platform of the suturing and cutting apparatus, the pushing block 82 is forced to push towards the distal end thereof, the second guiding portion 812 (bump) of the pressing block 81 moves along the first guiding portion 821 (the first slope) of the pushing block 82, as the first slope inclines upwards from the distal end to the proximal end, hence, the bump is lifted during the process of the pushing block 82 moving from the third position to the fourth position, accordingly, the second blocking portion 811 locates at the distal end of the pressing block 81 is lifted too, the pressing block 81 rotates from the first position to the second position around the pin 9 (that is rotating from the position shown in FIG. 4 to the position shown in FIG. 6). As shown in FIG. 6, this time, the second blocking portion 811 of the pressing block 81 departs from the first blocking portion 63 of the cutter pushing rod 6, the cutter pushing rod 6 is under the unlocking status, and is movable towards the distal end under the action of the actuating assembly. When the stapling head assembly is removed from the platform of the suturing and cutting apparatus after the suturing and cutting apparatus is fired, the pushing block 82 loses the action of external force, and the pushing block 82 moves back to the third position under the action of the spring 84, this time, the pressing block 81 moves from the proximal end to the distal end of the pushing block 82, and the pressing block 81 rotates back to the first position under the action of the torsional spring 83.

In one embodiment, there may be a third guiding portion 64 set at the proximal end 61 of the cutter pushing rod 6, when the cutter pushing rod 6 moves towards the proximal end, the third guiding portion 64 can guide the pressing block 81 to rotate from the first position to the second position. The third guiding portion 64 may be a second slope (as shown in FIG. 4 or FIG. 6). Said second slope orients the proximal end 61 of the cutter pushing rod 6, and inclines downwards from the distal end to the proximal end. During the process of the cutter pushing rod 6 being reset and moving back to the proximal end, the second blocking portion 811 of the pressing block 81 is movable along the second slope to make the pressing block rotate from the first position to the second position, after the cutter pushing rod 6 is reset, the pressing block 81 rotates again to the first position under the action of the torsional spring 83, the second blocking portion 811 clamps again with the first blocking portion 63 of the cutter pushing rod 6, and makes the cutter pushing rod 6 be back to the locking status again. The second slope can make the reset of the cutter pushing rod 6 more convenient. The technicians in the art should understand that the third guiding portion 64 is not necessary, during the process of the reset of the cutter pushing rod 6, it can also be used that pull the cutter pushing rod 6 to be reset after pushing the pushing block 82 to make the pressing block 81 rotate to the fourth position. It won't be described in detail here.

The structure preventing from moving and being fired by mistake of the embodiment can only release the cutter pushing rod 6 to make it under the unlocking status by applying an external force to the pushing block 8 to push the pushing block 8 to move along the longitudinal direction and make the pressing block 81 rotate and lift; while under the condition that no external force is applied to the pushing block 8, the second blocking portion at the distal end of the pressing block 81 stays clamping with the first blocking portion of the cutter pushing rod 6, and the cutter pushing rod 6 is made to be under the unlocking status, so the movement and being fired by mistake of the cutter pushing rod 6 can be prevented.

The invention further provides a suturing and cutting apparatus for endoscopic surgery. The suturing and cutting apparatus comprises a body and the stapling head assembly. Wherein, the stapling head assembly is shown in FIG. 1 to FIG. 6. The connecting tube 5 of the stapling head assembly and the cutter pushing rod 6 connect to the body. The body can push the cutter pushing rod 6, and make the cutter 7 move towards the distal direction of the cartridge support 1.

Combining the embodiments shown in FIG. 1 to FIG. 6, the technicians in the art should understand, with the stapling head assembly and the suturing and cutting apparatus for endoscopic surgery of the invention, the cutter pushing rod can be effectively prevented from moving during the processes of assembling, packaging, transportation and so on before the cartridge assembly is mounted onto the instrument platform of the endoscopic stapler, the instrument platform can be made sure to be mounted correctly with the cutter pushing rod before operation, and the instrument can be prevented from being fired by mistake.

The specific embodiments of the invention are described above. It should be understood that, the invention is not limited to the specific embodiments above, and the technicians in the art can make all kinds of transformation and amendments within the scope of the claims, which will not affect the substantial contents of the invention.

What is claimed is:

1. A stapling head assembly comprising:
   a cartridge;
   a cartridge support detachably attached to the cartridge;
   a connecting tube including a distal end and a sidewall, the distal end being connected to a proximal end of said cartridge support, and the sidewall defining a first limiting groove longitudinally extending along a longitudinal direction of said connecting tube;
   a cutter pushing rod movably set inside said connecting tube; and
   a lockout mechanism connected to said connecting tube, said lockout mechanism including:
      a pressing block used to lock a proximal end of said cutter pushing rod to prevent said cutter pushing rod from moving before said stapling head assembly is used, said pressing block being rotatable between a first position and a second position relative to said connecting tube;
      a pushing block adapted to move between a third position and a fourth position, and used to push said pressing block to rotate from said first position when in the third position and towards said second position when moving towards the fourth position, said pushing block located at one side of said pressing block, and movable between the third position and the fourth position relative to said connecting tube along a longitudinal direction of said connecting tube; and a pin adapted to rotatably connect said pressing block to said connecting tube, wherein said pressing block connects to an inside of said first limiting groove by the pin, and said pressing block is rotatable around said pin relative to said connecting tube.

2. The stapling head assembly according to claim 1, wherein, a first blocking portion is set at the proximal end of the cutter pushing rod, a second blocking portion is set on said pressing block, when said pressing block is located at said first position, said second blocking portion clamps with said first blocking portion, said cutter pushing rod cannot move under the locking status; when said pressing block rotates to said second position, said second blocking portion departs from said first blocking portion, said cutter pushing rod is under an unlocking status and is movable along the longitudinal direction.

3. The stapling head assembly according to claim 2, wherein, a proximal end of said pressing block connects to said connecting tube by said pin, said second blocking portion is set at a distal end of said pressing block.

4. The stapling head assembly according to claim 2, wherein, there is further a second limiting groove set on said connecting tube along the longitudinal direction of the connecting tube, said second limiting groove is set at one side of said first limiting groove, and communicates to said first limiting groove, said pushing block is set inside said second limiting groove, and is moveable between said third position and the fourth position along said second limiting groove.

5. The stapling head assembly according to claim 1, wherein, said pushing block is set at a periphery of the connecting tube, when said pushing block moves from said third position to said fourth position, the pressing block is pushed to rotate from said first position to said second position.

6. The stapling head assembly according to claim 1, wherein, said lockout mechanism further comprises:

a torsional spring connecting said pressing block and said connecting tube, and actuating said pressing block to rotate from said second position to said first position; and a spring connecting said pushing block and said connecting tube, and actuating said pushing block to move from said fourth position towards said third position.

7. The stapling head assembly according to claim 6, wherein, a proximal end of said spring connects to a distal end of said pushing block, and a distal end of said spring connects to said connecting tube.

8. The stapling head assembly according to claim 6, wherein, one of said distal and proximal ends of said torsional spring connects to said pressing block, and the other of said distal and proximal ends of said torsional spring connects to an inner wall of said connecting tube.

9. The stapling head assembly according to claim 1, wherein said pushing block includes a first guiding portion at an outer surface of said pushing block, said pressing block includes a second guiding portion set at a side wall of one side of a distal end of said pressing block close to said pushing block, said second guiding portion is set at an outer surface of said pushing block, when said pushing block moves from said third position to said fourth position, said first guiding portion pushes said second guiding portion, so said pressing block rotates from said first position to said second position.

10. The stapling head assembly according to claim 9, wherein, said first guiding portion is a first slope, said first slope orients to a distal end of said pushing block, and inclines upwards from the distal end to a proximal end of said pushing block.

11. The stapling head assembly according to claim 10, wherein, said second guiding portion is a bump set protruded at a side wall of the distal end of said pressing block.

12. The stapling head assembly according to claim 11, wherein said cutter pushing rod includes a third guiding portion set at the proximal end of said cutter pushing rod, when said cutter pushing rod moves to the proximal end of said connecting tube, said third guiding portion guides said pressing block to rotate from said first position to the second position.

13. The stapling head assembly according to claim 12, wherein, said third guiding portion is a second slope, said second slope orients towards said proximal end of said cutter pushing rod, and inclines downwards from a distal end to said proximal end of said cutter pushing rod.

14. A suturing and cutting apparatus for endoscopic surgery comprising:

a body; and a stapling head assembly including a cartridge, a cartridge support detachably attached to the cartridge, a connecting tube having a distal end connected to a proximal end of said cartridge support, a cutter pushing rod movably set inside said connecting tube, and a lockout mechanism connected to said connecting tube, said lockout mechanism including:

a pressing block used to lock a proximal end of said cutter pushing rod to prevent said cutter pushing rod from moving before said stapling head assembly is used, wherein said pressing block is rotatable between a first position and a second position relative to said connecting tube; and a pushing block used to push said pressing block to rotate from said first position towards said second position, a first limiting groove set at a side wall of said connecting tube along a longitudinal direction of said connecting tube, said pressing block connecting to an inside of said first limiting groove by a pin, and said pressing block being rotatable around said pin relative to said connecting tube, and wherein said pushing block, located at one side of said pressing block, is movable between a third position and a fourth position relative to said connecting tube along the longitudinal direction of said connecting tube, and the connecting tube and the cutter pushing rod are connected to said body.

15. The suturing and cutting apparatus according to claim 14, wherein a first blocking portion is set at a proximal end of the cutter pushing rod, a second blocking portion is set on said pressing block, when said pressing block is located at said first position, said second blocking portion clamps with said first blocking portion, said cutter pushing rod cannot move under a locking status; when said pressing block rotates to said second position, said second blocking portion departs from said first blocking portion, said cutter pushing rod is under an unlocking status and is movable along longitudinal direction.

16. The suturing and cutting apparatus according to claim 14, wherein, said pushing block is set at a periphery of the connecting tube, when said pushing block moves from said third position to said fourth position, the pressing block is pushed to rotate from said first position to said second position.

17. The suturing and cutting apparatus according to claim 14, wherein, there is further a second limiting groove set on said connecting tube along the longitudinal of said connecting tube, said second limiting groove is set at one side of said first limiting groove, and communicates to said first limiting groove, said pushing block is set inside said second limiting groove, and is moveable between said third position and the fourth position along said second limiting groove.

18. The suturing and cutting apparatus according to claim 14, wherein said lockout mechanism includes a torsional spring, connecting said pressing block and said connecting tube, and actuating said pressing block to rotate from said second position to said first position, and a spring connecting said pushing block and said connecting tube, and actuating said pushing block to move from said fourth position towards said third position.

\* \* \* \* \*